US006114562A

United States Patent [19]

[11] Patent Number: 6,114,562

[45] Date of Patent: Sep. 5, 2000

Fukuda et al.

[54] ORGANOSILICON COMPOUNDS AND METHOD OF MAKING

[75] Inventors: Kenichi Fukuda; Hirofumi Kishita, both of Usui-gun, Japan

[73] Assignee: Shin-Etsu Chemical Co., Ltd., Tokyo, Japan

[21] Appl. No.: 09/366,788

[22] Filed: Aug. 4, 1999

[30] Foreign Application Priority Data

Aug. 4, 1998 [JP] Japan .................................. 10-232252

[51] Int. Cl.[7] .................................. C02F 7/08; C02F 7/18

[52] U.S. Cl. ............................................ 556/485; 556/448

[58] Field of Search ..................................... 556/448, 485

[56] References Cited

U.S. PATENT DOCUMENTS

| | | | |
|---|---|---|---|
| 4,692,537 | 9/1987 | McAlister | 556/485 X |
| 5,011,963 | 4/1991 | Ogawa et al. | 556/485 |
| 5,834,612 | 11/1998 | Furukawa et al. | 556/448 |
| 5,869,728 | 2/1999 | Jenkner et al. | 556/485 X |

*Primary Examiner*—Paul F. Shaver
*Attorney, Agent, or Firm*—Millen, White, Zelano & Branigan, P.C.

[57] ABSTRACT

Novel organosilicon compounds having a perfluoroalkyl or perfluoropolyether group and at least one ethynyl group are useful as an agent for controlling hydrosilylation reaction between a —SiH group-bearing compound and a —CH=$CH_2$ group-bearing compound.

15 Claims, 2 Drawing Sheets

ORGANOSILICON COMPOUNDS AND METHOD OF MAKING

This invention relates to novel organosilicon compounds and more particularly, to fluorinated organosilicon compounds having at least one ethynyl group and useful as an agent for controlling hydrosilylation reaction. It also relates to a method for preparing the organosilicon compounds.

BACKGROUND OF THE INVENTION

Silicone rubber compositions of the addition curing type undergo crosslinking through hydrosilylation reaction represented by the following scheme as elementary reaction, converting into elastomers.

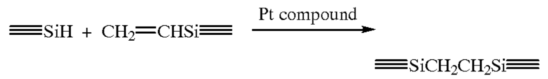

To control this reaction in order to insure a pot life or shelf life, a typical prior art practice uses ethynyl group-bearing compounds as shown below.

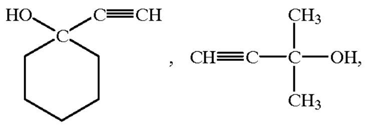

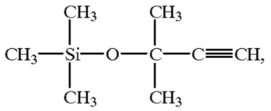

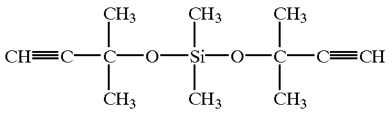

These compounds, however, are incompatible with fluorosilicones and perfluoropolymers having high fluorine contents and can introduce separation or non-uniformity into the reaction system.

SUMMARY OF THE INVENTION

An object of the invention is to provide a novel and improved organosilicon compound which is useful as an agent for controlling a hydrosilylation reaction between a —SiH group-bearing compound and a —CH=$CH_2$ group-bearing compound. More particularly, an object is to provide a novel and improved organosilicon compound which is fully compatible with fluorosilicones and perfluoropolymers having high fluorine contents so that it does not separate out therefrom and is effective for controlling an addition reaction.

Another object of the invention is to provide a method for preparing the organosilicon compound.

In one aspect, the invention provides a fluorinated organosilicon compound of formula (1) which is novel. In another aspect, the invention provides a method for preparing a fluorinated organosilicon compound of formula (1) by reacting a fluorinated chlorosilane of formula (2) with an ethynyl group-bearing alcohol of formula (3) as shown by the following reaction scheme. The fluorinated organosilicon compound of formula (1) is useful as an agent for controlling a hydrosilylation reaction.

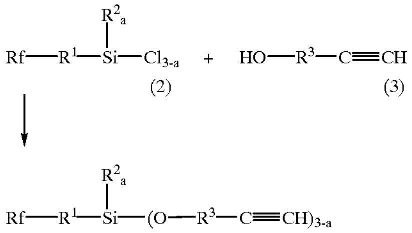

(2) (3)

(1)

In the formulae, Rf is a monovalent perfluoroalkyl or perfluoropolyether group, $R^1$ is a divalent organic group, $R^2$ is a monovalent hydrocarbon group, $R^3$ is a divalent hydrocarbon group, and a is equal to 0, 1 or 2.

DESCRIPTION OF THE PREFERRED EMBODIMENTS

Figure 1:
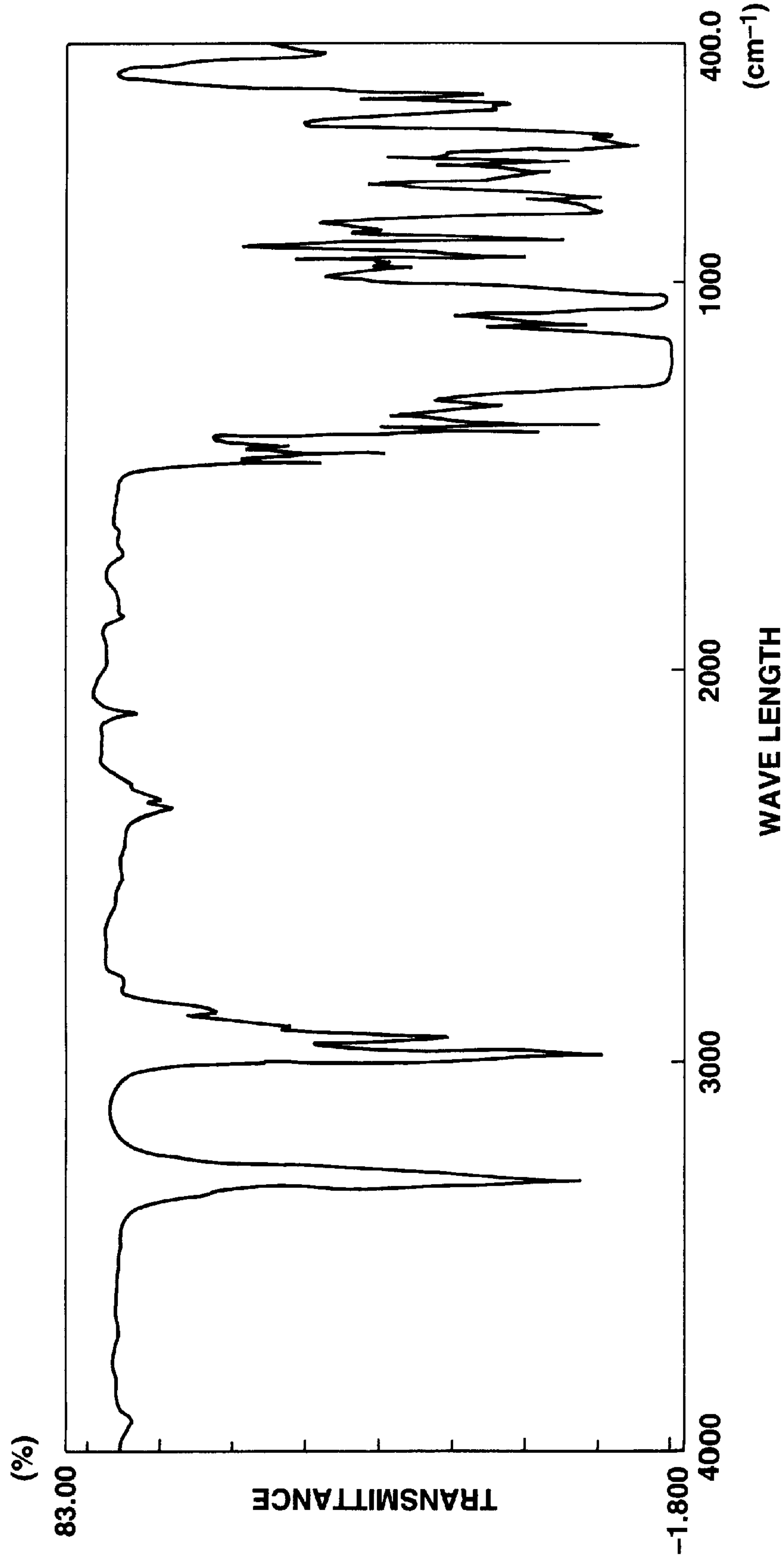
FIG. 1 is an IR spectrum of the compound synthesized in Example 1.

According to the invention, there are provided novel organosilicon compounds of the following general formula (1).

(1)

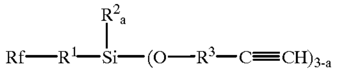

In formula (1), Rf is a monovalent perfluoroalkyl or perfluoropolyether group, which is exemplified by the following.

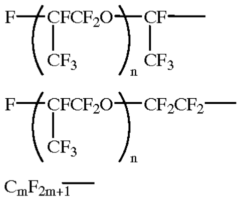

In the formulae, m is an integer of 1 to 15 and especially 3 to 10, and n is an integer of 1 to 8 and especially 1 to 5.

$R^1$ is a divalent organic group. Lower alkylene groups of 1 to 6 carbon atoms are preferred although $R^1$ is not limited thereto. The lower alkylene group of 1 to 6 carbon atoms may be separated by or terminated with an oxygen atom, nitrogen atom or carbonyl group. Exemplary alkylene groups are shown below.

$—(CH_2)_p—$ $—(CH_2)_q—O—CH_2—$ $-(CH_2)_p-$ $-(CH_2)_q-O-CH_2-$

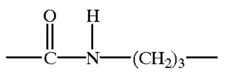

Herein, p is an integer of 1 to 6 and especially 2 to 4, and q is an integer of 0 to 5 and especially 2 to 4.

$R^2$ is a monovalent hydrocarbon group. Illustrative, non-limiting examples of the monovalent hydrocarbon group include lower alkyl groups of 1 to 6 carbon atoms such as methyl, ethyl, propyl, butyl, pentyl and hexyl, cycloalkyl groups such as cyclohexyl, aryl groups such as phenyl, and aralkyl groups such as benzyl.

$R^3$ is a divalent hydrocarbon group. Preferred, non-limiting examples of the group represented by $R^3$ are given below.

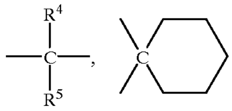

Herein, $R^4$ and $R^5$ are independently monovalent hydrocarbon groups, for example, alkyl groups of 1 to 10 carbon atoms, such as methyl, ethyl, propyl, butyl, isobutyl, hexyl, octyl and decyl.

The letter a is equal to 0, 1 or 2, indicating that the compound has at least one ethynyl group in one molecule.

The organosilicon compound of formula (1) can be synthesized, for example, by reacting a fluorinated chlorosilane with an ethynyl group-bearing alcohol in the presence of an acid acceptor such as urea.

The fluorinated chlorosilane serving as one reactant is preferably of the following general formula (2):

(2)

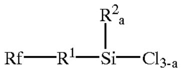

wherein Rf, $R^1$, $R^2$ and a are as defined above. Illustrative examples of the fluorinated chlorosilane are given below.

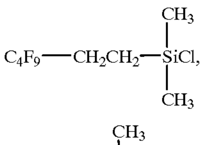

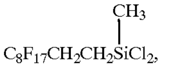

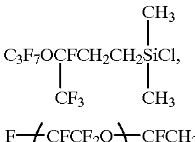

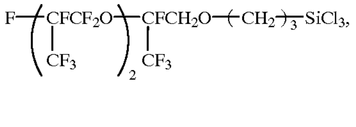

-continued

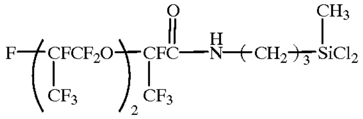

The ethynyl group-bearing alcohol serving as another reactant is preferably of the following general formula (3):

$$HO-R^3-C\equiv CH \quad (3)$$

wherein $R^3$ is as defined above. Illustrative examples of the alcohol are given below.

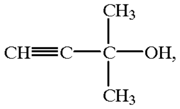

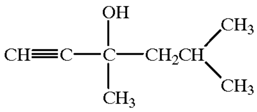

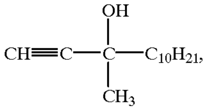

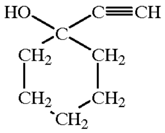

In the above reaction, the silane of formula (2) and the alcohol of formula (3) are preferably used in such amounts that 1 to 2 mol of the alcohol of formula (3) is available per mol of the chlorine atom in the silane of formula (2). The amount of the acid acceptor used is preferably 1 to 2 mol per mol of the chlorine atom in the silane of formula (2). A solventless system is preferred for convenience of progress to the subsequent step. Preferably reaction is effected in an inert gas atmosphere such as nitrogen and at a temperature from room temperature (20° C.) to 100° C. The reaction time is usually about 4 to about 24 hours.

The organosilicon compounds of the invention are used as an agent for controlling hydrosilylation reaction. Particularly for hydrosilylation reaction between an alkenyl group-bearing compound and an SiH group-bearing compound in the presence of a platinum group catalyst wherein either one or both of the alkenyl group-bearing compound and the SiH group-bearing compound contain fluorine atoms, the improved organosilicon compound is compatible with the relevant compounds and becomes an effective agent for controlling hydrosilylation reaction.

EXAMPLE

Examples of the invention are given below by way of illustration and not by way of limitation.

Example 1

A 100-ml, three-necked flask equipped with a stirrer, condenser, and thermometer was charged with 19.5 g (0.23 mol) of an ethynyl group-bearing compound of the following formula (4) and 19.5 g (0.21 mol) of urea, which were stirred. The flask was purged with nitrogen and heated to an internal temperature of 50° C. To the flask, 50.0 g (0.089 mol) of a fluorinated dichlorosilane of the following formula (5) was added dropwise from a dropping funnel.

(4)

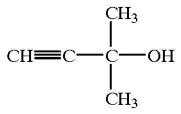

(5)

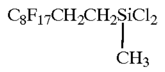

With the flask kept at an internal temperature of 60° C., the contents were stirred for 16 hours. The reaction solution was cooled, following which the lower layer was taken out. A similar flask was charged with the separated product, to which 0.3 g of propylene oxide was added for neutralization. The contents were stirred for one hour at 40° C.

The stirring step was followed by stripping at a bath temperature of 100° C. and a vacuum of 1 mmHg. After cooling, filtration under pressure was effected in order to remove the salt. The filtrate was distilled in vacuum, collecting 34.4 g of the compound shown below (yield 59%, b.p. 115° C./1 mmHg).

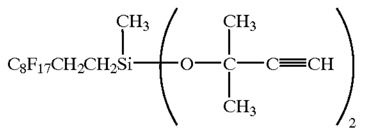

To confirm the molecular structure of the fraction, GC-MS analysis and IR spectroscopy were carried out, with the following results.

GCMS: $M^+$=656

IR spectrum: FIG. 1

$\nu_{\equiv CH}$: 3320 $cm^{-1}$, 640 $cm^{-1}$ $\nu_{C\equiv CH}$: 2100 $cm^{-1}$ Example 2

A flask as used in Example 1 was charged with 4.4 g (0.052 mol) of the ethynyl group-bearing compound used in Example 1 and 3.0 g (0.049 mol) of urea. The flask was purged with nitrogen and heated to an internal temperature of 50° C. To the flask, 17.8 g (0.0395 mol) of a fluorinated chlorosilane of the following formula (6) was added dropwise from a dropping funnel.

(6)

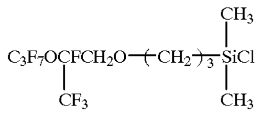

After 7 hours of reaction, the reaction solution was cooled, following which the lower layer was taken out. As in Example 1, 0.04 g of propylene oxide was added to the separated product for neutralization.

Post-treatment as in Example 1 was followed by vacuum distillation to collect 8.4 g of the compound shown below (yield 42%, b.p. 90° C./3 mmHg).

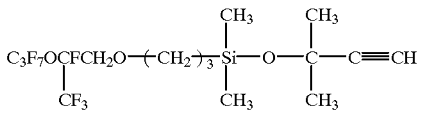

To confirm the molecular structure of the fraction, GC-MS analysis and IR spectroscopy were carried out, with the following results.

GCMS: $M^+$=498

Figure 2:
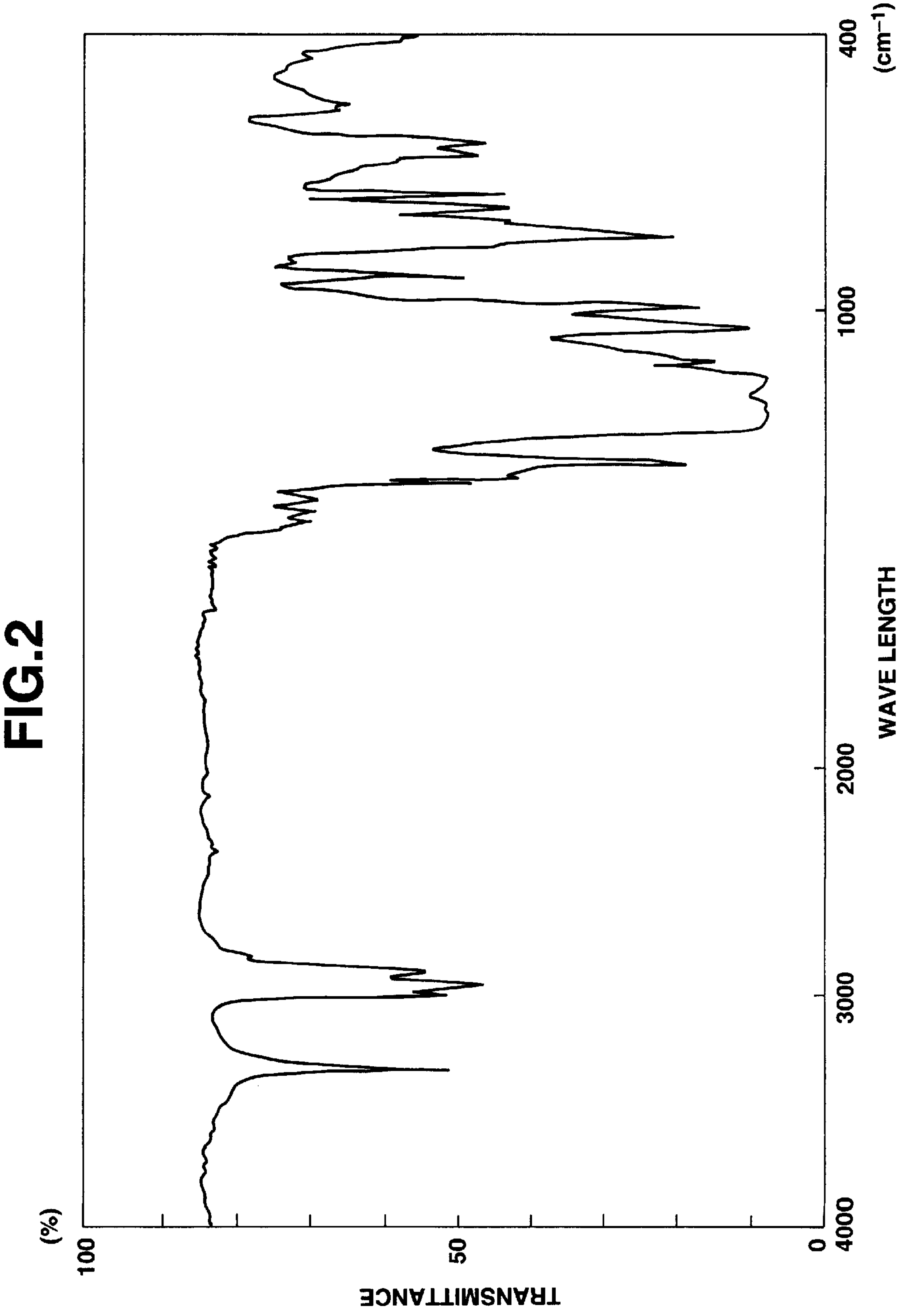
FIG. 2 is an IR spectrum of the compound synthesized in Example 2.

IR spectrum: FIG. 2

$\nu_{\equiv CH}$: 3320 $cm^{-1}$, 640 $cm^{-1}$ $\nu_{C\equiv CH}$: 2100 $cm^{-1}$ The novel and improved organosilicon compound is useful as an agent for controlling hydrosilylation reaction between a —SiH group-bearing compound and a —CH=$CH_2$ group-bearing compound. Since the organosilicon compound is fully compatible with fluorosilicones and perfluoropolymers having high fluorine contents, it does not separate out therefrom and is highly effective for controlling addition reaction.

Japanese Patent Application No. 10-232252 is incorporated herein by reference.

The invention has been described in detail with particular reference to preferred embodiments thereof, but it will be understood that variations and modifications can be effected within the spirit and scope of the invention.

We claim:

1. An organosilicon compound of formula (1):

(1)

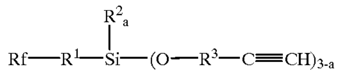

wherein Rf is a monovalent perfluoroalkyl or perfluoropolyether group, $R^1$ is a divalent organic group, $R^2$ is a monovalent hydrocarbon group, $R^3$ is a divalent hydrocarbon group, and a is equal to 0, 1 or 2.

2. A method for preparing an organosilicon compound of formula (1):

(1)

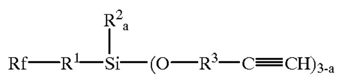

wherein Rf is a monovalent perfluoroalkyl or perfluoropolyether group, $R^1$ is a divalent organic group, $R^2$ is a monovalent hydrocarbon group, $R^3$ is a divalent hydrocarbon group, and a is equal to 0, 1 or 2, said method comprising the step of reacting a fluorinated chlorosilane of formula(2):

(2)

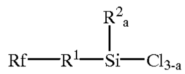

wherein Rf, $R^1$, $R^2$ and a are as defined above with an ethynyl group-bearing alcohol of formula (3):

$HO—R^3—C≡CH$ (3)

wherein $R^3$ is as defined above.

3. The organosilicon compound of claim 1, wherein Rf is

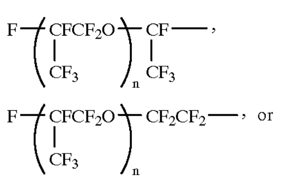

$C_mF_{2m+1}—$ wherein m is an integer of 1 to 15, and n is an integer of 1 to 8.

4. The organosilicon compound of claim 3, wherein m is an integer of 3 to 10, and n is an integer of 1 to 5.

5. The organosilicon compound of claim 1, wherein $R^1$ is an alkylene group of 1 to 6 carbon atoms, which is optionally separated by or terminated with an oxygen atom, nitrogen atom or carbonyl group.

6. The organosilicon compound of claim 1, wherein $R^1$ is $—(CH_2)_p—$, $—(CH_2)_q—O—CH_2—$, or

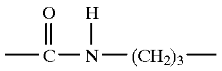

wherein p is an integer of 1 to 6 and q is an integer of 0 to 5.

7. The organosilicon compound of claim 6, wherein p is an integer of 2 to 4, and q is an integer of 2 to 4.

8. The organosilicon compound of claim 1, wherein $R^2$ is an alkyl group of 1 to 6 carbon atoms, a cycloalkyl group, an aryl group or an aralkyl group.

9. The organosilicon compound of claim 8, wherein $R^2$ is methyl, ethyl, propyl, butyl, pentyl, hexyl, cyclohexyl, phenyl or bentyl.

10. The organosilicon compound of claim 1, wherein $R^3$ is

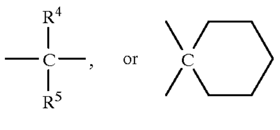

and, wherein $R^4$ and $R^5$ are independently monovalent hydrocarbon groups.

11. The organosilicon compound of claim 10, wherein $R^4$ and $R^5$ are alkyl groups of 1 to 10 carbon atoms.

12. The method according to claim 2, wherein the fluorinated chlorosilane is

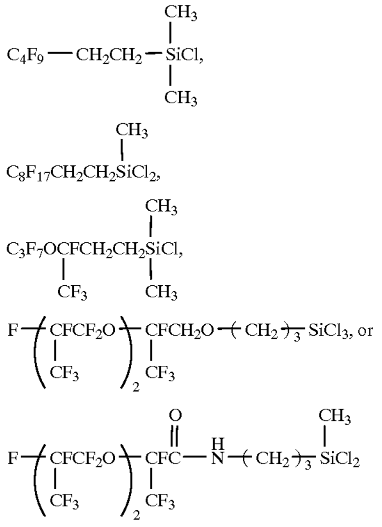

13. The method according to claim 2, wherein the ethynyl group-bearing alcohol

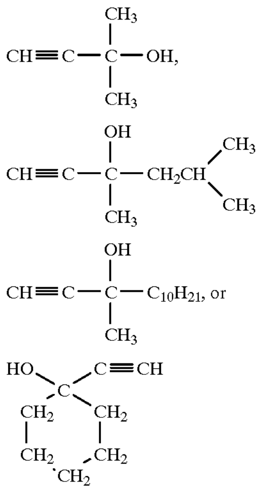

14. The method according to claim 2, wherein the amounts of the silane of formula (2) and the alcohol of formula (3) are such that the molar ratio of the available alcohols of formula (3) to the chlorine atom in the silane of formula (2) is 1 to 2.

15. The method according to claim 2, wherein the reaction is carried out in an inert gas atmosphere, at a temperature of 20°C. to 100°C., and for about 4 to about 24 hours.

* * * * *